US009949699B2

(12) United States Patent
Visser et al.

(10) Patent No.: US 9,949,699 B2
(45) Date of Patent: Apr. 24, 2018

(54) TOMOGRAPHIC IMAGE GENERATING SYSTEM COMPRISING A THREE-DIMENSIONAL CAMERA FOR AQUIRING A THICKNESS AND/OR A TWO-DIMENSIONAL SHAPE OF A SURFACE OF A SUBJECT

(71) Applicant: Konica Minolta, Inc., Chiyoda-ku, Tokyo (JP)

(72) Inventors: Emiel Visser, Hino (JP); Youichi Ono, Akiruno (JP); Ko Matsui, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 98 days.

(21) Appl. No.: 14/803,745

(22) Filed: Jul. 20, 2015

(65) Prior Publication Data
US 2016/0019701 A1  Jan. 21, 2016

(30) Foreign Application Priority Data

Jul. 18, 2014  (JP) .................................. 2014-147451

(51) Int. Cl.
*A61B 6/03* (2006.01)
*A61B 6/04* (2006.01)
(Continued)

(52) U.S. Cl.
CPC ............ *A61B 6/025* (2013.01); *A61B 5/0059* (2013.01); *A61B 6/032* (2013.01); *A61B 6/06* (2013.01);
(Continued)

(58) Field of Classification Search
CPC ..................................................... A61B 6/025
(Continued)

(56) References Cited

U.S. PATENT DOCUMENTS 4,349,740 A * 9/1982 Grassmann .............. A61B 6/02
                                                      378/134
6,215,848 B1 * 4/2001 Linders .................. A61B 6/481
                                                      250/370.09
(Continued)

FOREIGN PATENT DOCUMENTS

JP   H03224545 A   10/1991
JP   2010005157 A   1/2010
(Continued)

OTHER PUBLICATIONS

Notification of Refusal for corresponding JP Application No. 2014-147451; dated Feb. 6, 2018.

*Primary Examiner* — Allen C. Ho
(74) *Attorney, Agent, or Firm* — Cantor Colburn LLP

(57) ABSTRACT

An embodiment of an tomographic image generating system may include: an imaging member that includes a radiation source, a radiation detector and a subject table, and captures the projected image a predetermined number of times while changing a positional relationship between the radiation source and the radiation detector; a reconstructing member that generates a tomographic image of the subject from the projected image captured by the imaging member; an acquiring member that acquires a thickness of the subject and/or a two-dimensional shape of a surface of the subject, the surface of the subject being irradiated with radiation; and a controlling member that determines an imaging condition for the imaging member and/or a reconstructing condition for the reconstructing member generating the tomographic image of the subject, on the basis of the thickness and/or the two-dimensional shape of the subject acquired by the acquiring member.

16 Claims, 8 Drawing Sheets

(51) Int. Cl.
*A61B 6/02* (2006.01)
*G06T 11/00* (2006.01)
*A61B 6/00* (2006.01)
*A61B 6/06* (2006.01)
*A61B 5/00* (2006.01)

(52) U.S. Cl.
CPC .......... *A61B 6/4208* (2013.01); *A61B 6/4233* (2013.01); *A61B 6/4241* (2013.01); *A61B 6/5205* (2013.01); *A61B 6/54* (2013.01); *A61B 6/542* (2013.01); *A61B 6/544* (2013.01); *A61B 6/545* (2013.01); *A61B 6/56* (2013.01); *A61B 6/563* (2013.01); *A61B 6/566* (2013.01); *G06T 11/003* (2013.01); *G06T 2211/40* (2013.01)

(58) Field of Classification Search
USPC .............................. 378/22, 25–27, 196, 197
See application file for complete search history.

(56) References Cited

U.S. PATENT DOCUMENTS

| | | | | |
|---|---|---|---|---|
| 6,222,902 B1* | 4/2001 | Lin | .................. | A61B 6/032 378/22 |
| 6,236,708 B1* | 5/2001 | Lin | .................. | A61B 6/025 378/22 |
| 6,292,534 B1* | 9/2001 | Linders | ................ | A61B 6/4233 348/E5.086 |
| 6,341,156 B1* | 1/2002 | Baetz | .................. | A61B 6/02 378/196 |
| 6,570,954 B2* | 5/2003 | Rasche | ................ | A61B 6/0457 378/21 |
| 6,707,878 B2* | 3/2004 | Claus | .................. | G06T 11/005 378/210 |
| 6,751,285 B2* | 6/2004 | Eberhard | ............... | A61B 6/502 378/37 |
| 6,914,958 B2* | 7/2005 | Ganin | .................. | A61B 6/032 378/26 |
| 6,925,144 B2* | 8/2005 | Matsumoto | ............ | A61B 6/032 378/22 |
| 6,940,943 B2* | 9/2005 | Claus | .................. | A61B 6/025 378/197 |
| 6,970,531 B2* | 11/2005 | Eberhard | ............... | A61B 6/563 378/197 |
| 6,973,160 B2* | 12/2005 | Matsumoto | ............. | A61B 6/02 348/E5.086 |
| 7,123,683 B2* | 10/2006 | Tsujii | .................. | A61B 6/4429 378/196 |
| 7,139,364 B2* | 11/2006 | Matsumoto | ............. | A61B 6/02 348/E5.086 |
| 7,356,113 B2* | 4/2008 | Wu | ........................ | A61B 6/025 378/22 |
| 7,515,682 B2* | 4/2009 | Li | .......................... | A61B 6/025 378/210 |
| 7,646,902 B2* | 1/2010 | Chan | ........................ | G06K 9/00 382/128 |
| 7,653,229 B2* | 1/2010 | Kaufhold | .............. | G06T 11/006 378/21 |
| 7,773,721 B2* | 8/2010 | Wu | ........................ | A61B 6/025 378/21 |
| 7,978,886 B2* | 7/2011 | Claus | .................... | G06T 11/006 382/128 |
| 8,184,765 B2* | 5/2012 | Akahori | ................. | A61B 6/032 378/25 |
| 8,411,923 B2* | 4/2013 | Ludwig | .................. | A61B 6/502 378/4 |
| 8,559,593 B2* | 10/2013 | Akahori | ................. | A61B 6/032 378/115 |
| 8,634,622 B2* | 1/2014 | Woods | ................ | G06K 9/3233 382/131 |
| 8,675,814 B2* | 3/2014 | Akahori | ................. | A61B 6/032 378/196 |
| 8,737,562 B2* | 5/2014 | Notohara | ............. | A61B 6/4291 378/26 |
| 8,768,026 B2* | 7/2014 | Ren | ...................... | A61B 6/0414 382/131 |
| 8,798,231 B2* | 8/2014 | Notohara | ............. | A61B 6/025 378/22 |
| 8,948,339 B2* | 2/2015 | Notohara | ................ | A61B 6/06 378/21 |
| 9,123,108 B2* | 9/2015 | Tajima | .................... | G06T 7/003 |
| 9,147,269 B2* | 9/2015 | Sakimoto | ................ | A61B 6/03 |
| 9,275,478 B2* | 3/2016 | Jerebko | ................. | G06T 11/005 |
| 9,361,711 B2* | 6/2016 | Jerebko | ................. | G06T 11/006 |
| 9,380,985 B2* | 7/2016 | Akahori | ................. | A61B 6/025 |
| 9,418,415 B2* | 8/2016 | Yamamoto | ........... | G06T 7/0012 |
| 9,675,277 B2* | 6/2017 | Arai | ...................... | A61B 5/1075 |

FOREIGN PATENT DOCUMENTS

| | | |
|---|---|---|
| JP | 2010233762 A | 10/2010 |
| JP | 2011087917 A | 5/2011 |

* cited by examiner

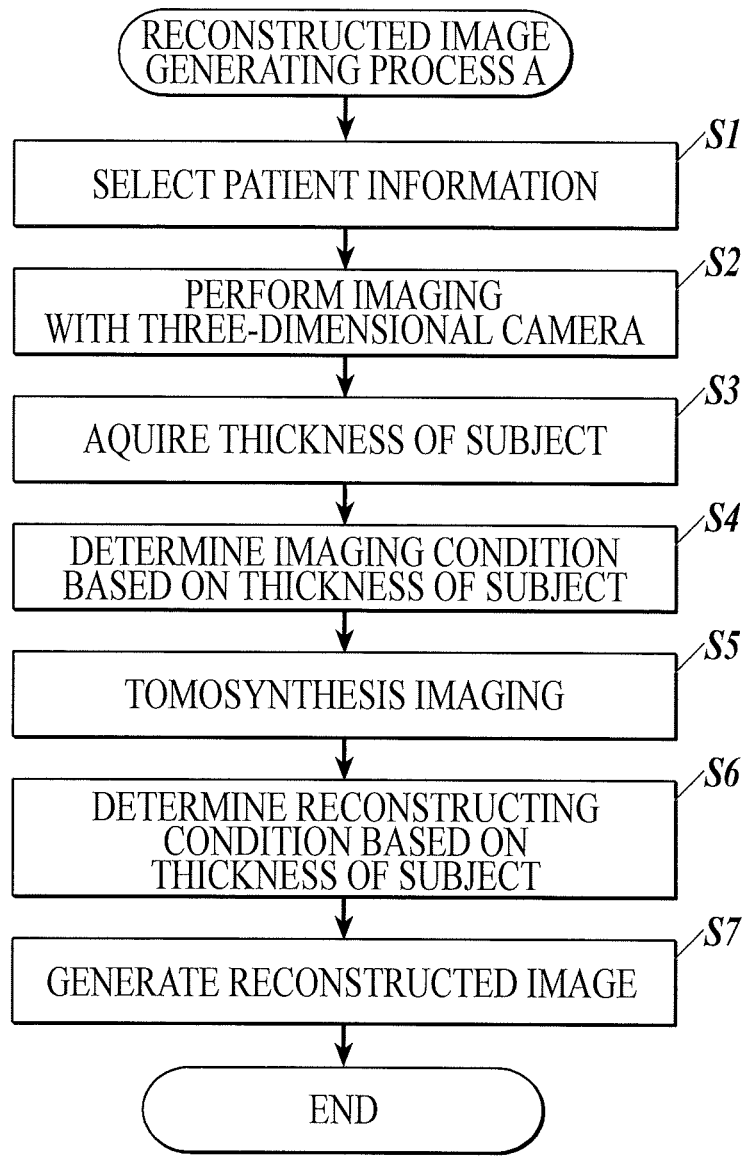

FIG.5A
FIG.5B
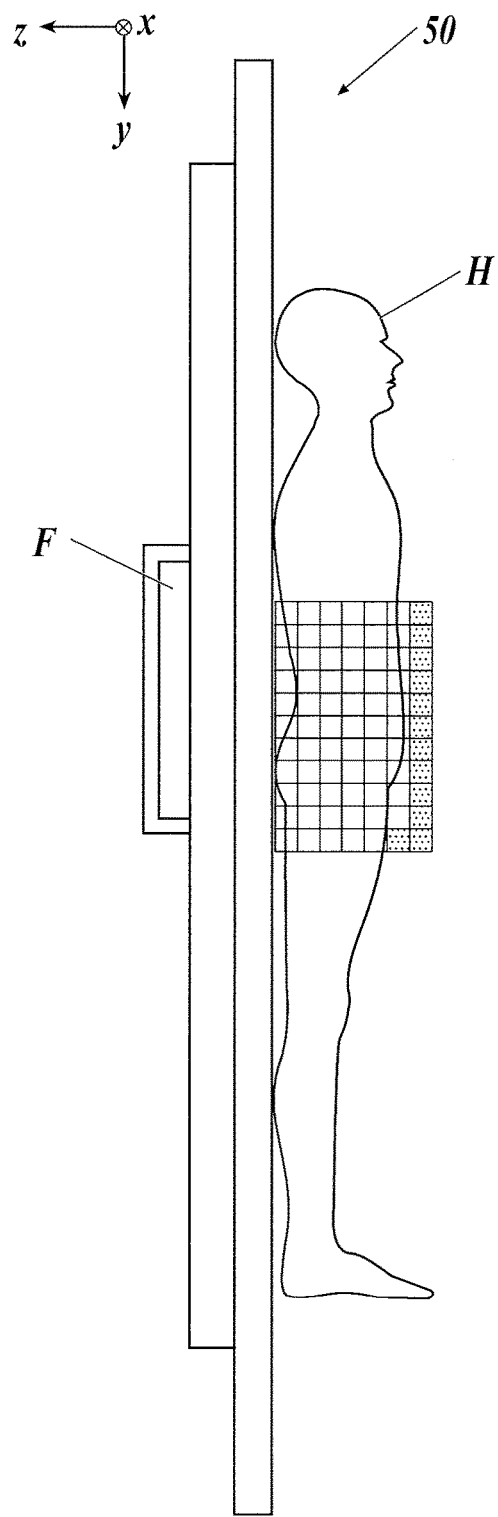
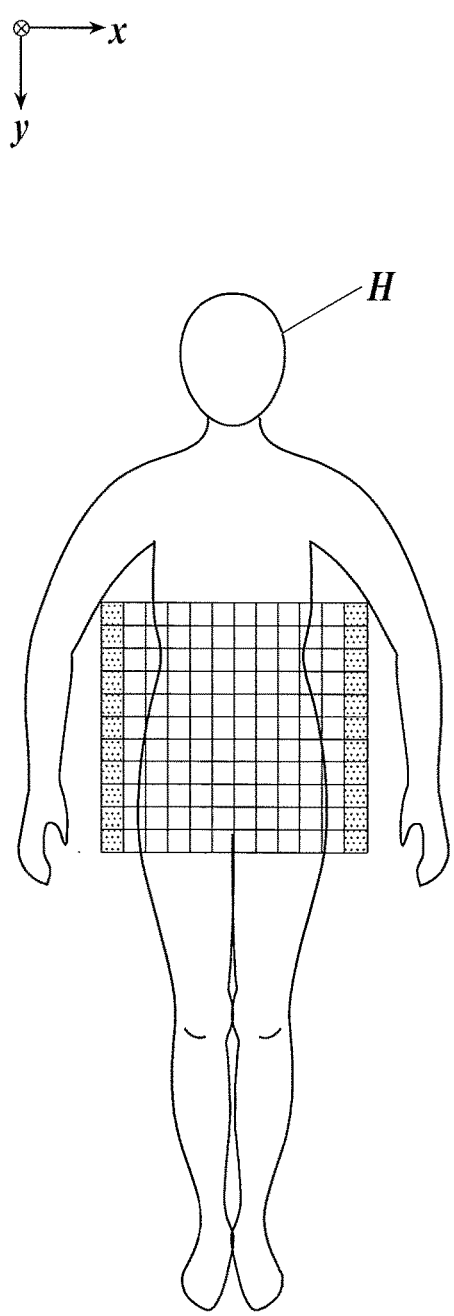

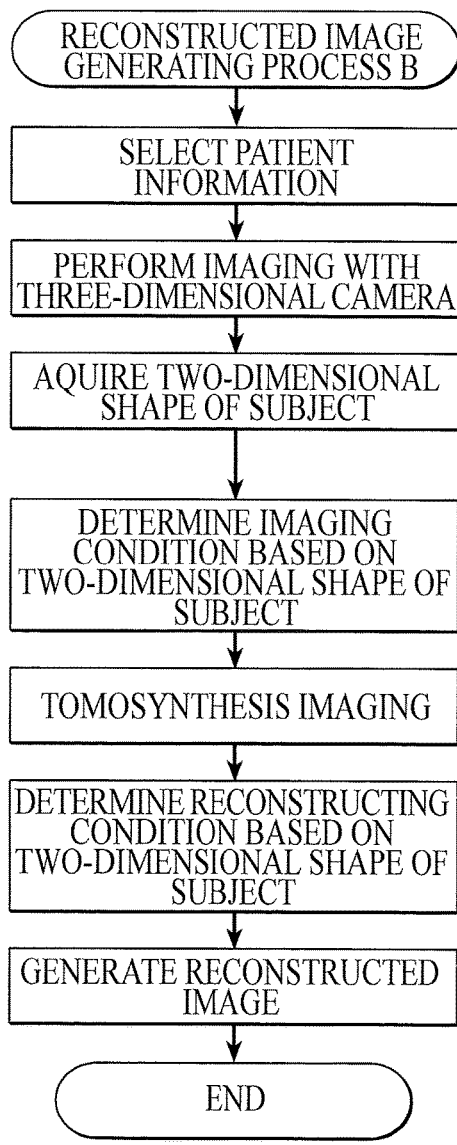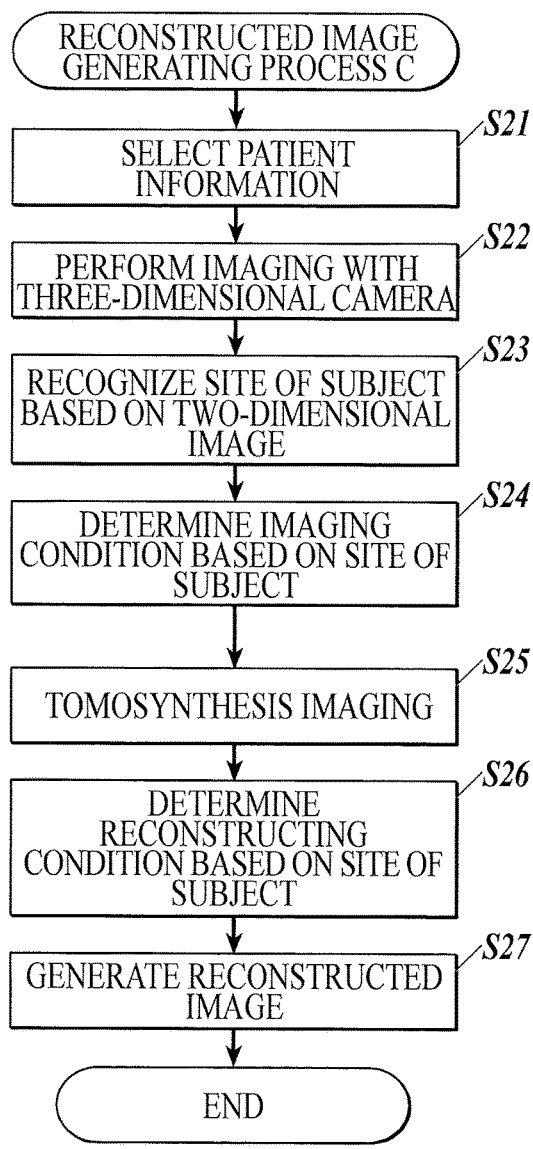

TOMOGRAPHIC IMAGE GENERATING SYSTEM COMPRISING A THREE-DIMENSIONAL CAMERA FOR AQUIRING A THICKNESS AND/OR A TWO-DIMENSIONAL SHAPE OF A SURFACE OF A SUBJECT

CROSS REFERENCE TO RELATED APPLICATIONS

The present invention claims priority under 35 U.S.C. § 119 to Japanese Application No. 2014-147451, filed Jul. 18, 2014, the entire content of which is incorporated herein by reference.

BACKGROUND OF THE INVENTION

Field of the Invention

The present invention relates to a tomographic image generating system.

Description of Related Art

In recent years, there has been used in the medical field a radiographic imaging apparatus which performs tomosynthesis imaging by irradiating a body of a patient, i.e. a subject, with radiation, converting the radiation passing through the subject into electrical signals, and acquiring the converted electrical signals as projected images. An image processing apparatus reconstructs a plurality of projected images of the subject acquired with the radiographic imaging apparatus so as to produce a two-dimensional tomographic image of the subject in a predetermined cross section (e.g. see Japanese Patent Application Laid-Open Publication No. 2010-233762).

The tomosynthesis imaging requires the determination of various imaging conditions including a swing angle of a radiation source, travel speeds of the radiation source and a radiation detector, a center of rotation, and the number of times of imaging. Likewise, the reconstruction of images requires the determination of various reconstructing conditions including a range of reconstruction, in-plane resolution, a slice pitch, and parameters for determining tomographic slice thickness.

These imaging and reconstructing conditions are determined and entered by a radiological technician or another radiographer. Unfortunately, determining and entering such imaging and reconstructing conditions require knowledge and expertise, and involve complicated and time-consuming operations.

SUMMARY

At least an embodiment of the present invention enables automatic determination of imaging and reconstructing conditions in tomosynthesis imaging to reduce a workload of a radiographer.

To achieve the above, a tomographic image generating system in which one aspect of the present invention is reflected includes: an imaging member that includes a radiation source for emitting radiation to a subject, a radiation detector including a two-dimensional array of radiation detecting elements each detecting the radiation to generate an electrical signal, the radiation detector acquiring a projected image in proportion to the emitted radiation, and a subject table for holding the subject, the subject table being disposed between the radiation source and the radiation detector, and that captures the projected image a predetermined number of times while changing a positional relationship between the radiation source and the radiation detector; a reconstructing member that generates a tomographic image of the subject from the projected image captured by the imaging member; an acquiring member that acquires a thickness of the subject and/or a two-dimensional shape of a surface of the subject, the surface of the subject being irradiated with radiation; and a controlling member that determines an imaging condition for the imaging member and/or a reconstructing condition for the reconstructing member generating the tomographic image of the subject, on the basis of the thickness and/or the two-dimensional shape of the subject acquired by the acquiring member.

Preferably, the controlling member determines, as the imaging condition, at least one of a swing angle of the radiation source, travel speeds of the radiation source and the radiation detector, a rotation center, a number of times of imaging, a radiation integration time of the radiation detector, and an irradiation time per projection, on the basis of a typical value of the thickness of the subject acquired by the acquiring member.

Preferably, the controlling member determines, as the imaging condition, at least one of an irradiation field of the radiation source, a swing angle of the radiation source, travel speeds of the radiation source and the radiation detector, a rotation center, a number of times of imaging, a radiation integration time of the radiation detector, and an irradiation time per projection, on the basis of a distribution of the thickness of the subject acquired by the acquiring member.

Preferably, the controlling member determines an irradiation field of the radiation source on the basis of the two-dimensional shape of the subject acquired by the acquiring member.

Preferably, the controlling member determines, as the reconstructing condition, at least one of a reconstruction range of the subject, a slice pitch, a parameter for determining a tomographic slice thickness, and a number of iteration in Iterative Reconstruction, on the basis of a typical value of the thickness of the subject acquired by the acquiring member.

Preferably, the controlling member further determines a value of a detection probability to be used for generating the tomographic image of the subject by the Iterative Reconstruction by the reconstructing member, on the basis of the typical value of the thickness of the subject acquired by the acquiring member.

Preferably, the controlling member determines, as the reconstructing condition, at least one of a reconstruction range of the subject, an in-plane resolution, a slice pitch, a parameter for determining a tomographic slice thickness, and a number of iteration in Iterative Reconstruction, on the basis of a distribution of the thickness of the subject acquired by the acquiring member.

Preferably, the controlling member further determines a value of a detection probability to be used for generating the tomographic image of the subject by the Iterative Reconstruction by the reconstructing member, on the basis of the distribution of the thickness of the subject acquired by the acquiring member.

Preferably, the controlling member further specifies an area containing no subject in the tomographic image to set a predetermined value to a pixel value of the specified area, on the basis of the distribution of the thickness of the subject acquired by the acquiring member.

Preferably, the controlling member determines, as the reconstructing condition, at least one of a reconstruction range of the subject, an in-plane resolution, and a number of iteration in Iterative Reconstruction, on the basis of the two-dimensional shape of the subject acquired by the acquiring member.

Preferably, the controlling member further specifies an area containing no subject in the tomographic image to set a predetermined value to a pixel value of the specified area, on the basis of the two-dimensional shape of the subject acquired by the acquiring member.

Preferably, the controlling member recognizes a site of the subject on the basis of the two-dimensional shape of the subject acquired by the acquiring member, and determines the imaging condition for the imaging member and/or the reconstructing condition for the reconstructing member on the basis of the recognized site.

Preferably, the controlling member recognizes the site of the subject and an imaging direction on the basis of the two-dimensional shape of the subject acquired by the acquiring member, and determines the imaging condition for the imaging member and/or the reconstructing condition for the reconstructing member generating the tomographic image of the subject, on the basis of the recognized site and imaging direction.

Preferably, the controlling member determines, as the imaging condition, at least one of a swing angle of the radiation source, travel speeds of the radiation source and the radiation detector, a rotation center, a number of times of imaging, a Source Image receptor Distance (SID), a radiation integration time of the radiation detector, an irradiation time per projection, and a binning size of the radiation detector.

Preferably, the controlling member determines, as the reconstructing condition, at least one of an in-plane resolution, a slice pitch, a parameter for determining a tomographic slice thickness, a parameter for determining a sharpness and/or granularity, and a number of iteration in Iterative Reconstruction.

Preferably, the tomographic image generating system further includes; a storing member that stores information on the thickness and/or the two-dimensional shape of the subject acquired by the acquiring member in association with patient information and site information on the subject; and a retrieving member that retrieves the patient information and the site information on the subject who is to be imaged, and when the storing member stores information corresponding to the patient information and the site information on the subject who is to be imaged, the controlling member determines the imaging condition and/or the reconstructing condition using the information on the thickness and/or the two-dimensional shape of the subject stored in the storing member in association with the patient information and the site information on the subject who is to be imaged, without acquisition by the acquiring member.

The present invention enables automatic determination of imaging and reconstructing conditions in tomosynthesis imaging, which reduces a workload of a radiographer.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 4 is a flowchart illustrating a reconstructed image generating process A executed by a control section of FIG. 3;

FIG. 5A is a diagram for explaining about a reconstruction range of a subject in a thickness direction;

FIG. 5B is a diagram for explaining about a reconstruction range of a subject in a plane irradiated with radiation;

FIG. 9 is a flowchart illustrating a reconstructed image generating process B executed by the control section of FIG. 3; and FIG. 10 is a flowchart illustrating a reconstructed image generating process C executed by the control section of FIG. 3.

PREFERRED EMBODIMENTS OF THE PRESENT INVENTION

Figure 1:
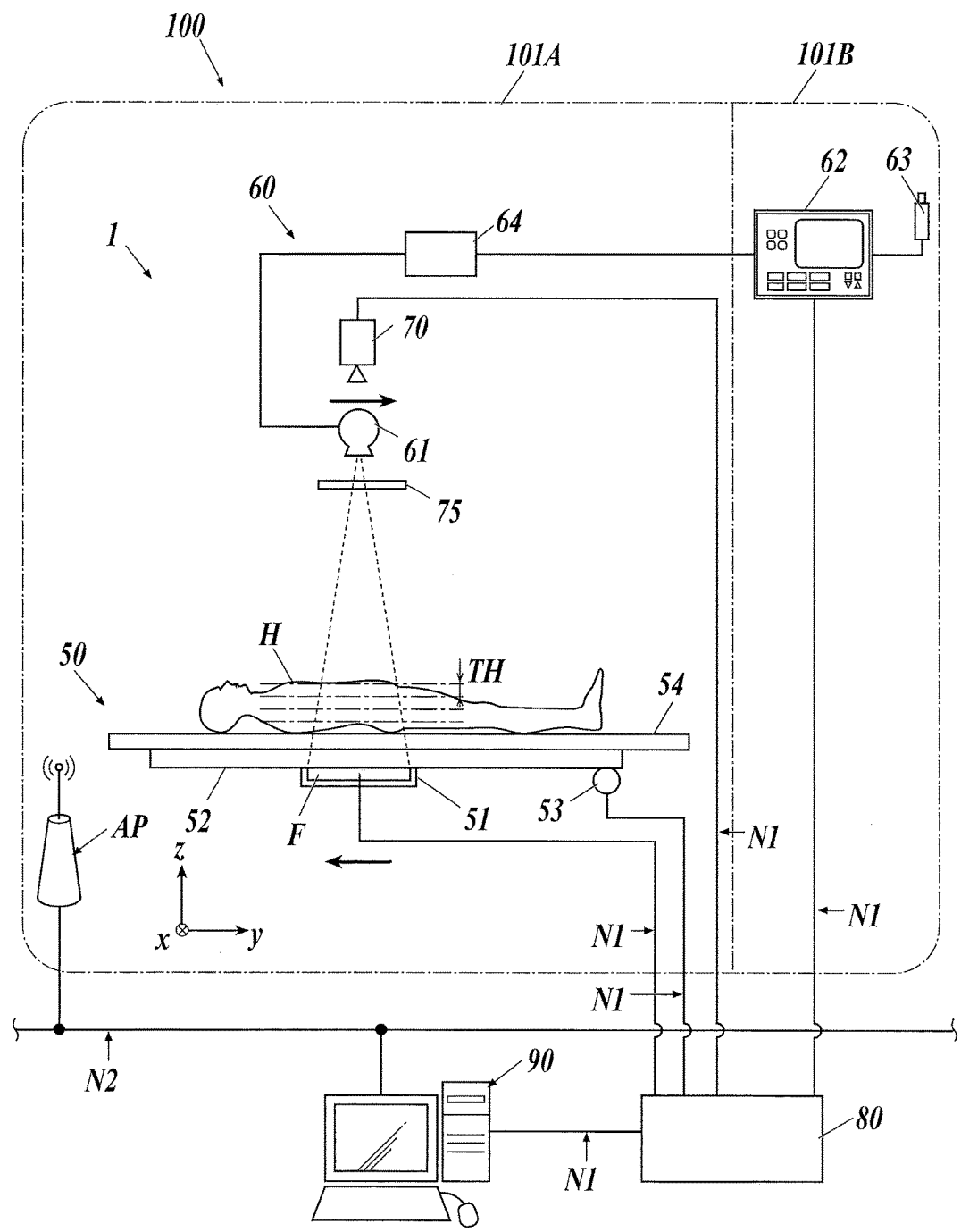
FIG. 1 is an overall view of a tomographic image generating system according to an embodiment.

Preferred embodiments of the present invention will now be described in detail with reference to the attached drawings. The scope of the present invention, however, should not be limited to examples depicted in the drawings.

First Embodiment

[Configuration of Tomographic Image Generating System 100]

The skeleton framework of a tomographic image generating system 100 according to a first embodiment will now be described. The tomographic image generating system 100 generates a tomographic image of a subject H (a part of the human body) by reconstructing projected images acquired through the tomosynthesis imaging of the subject H. FIG. 1 is a schematic view of the tomographic image generating system 100 according to this embodiment. With reference to FIG. 1, the tomographic image generating system 100 mainly includes a radiographic imaging apparatus 1 and a console 90.

In the embodiments described below, a longitudinal direction of a subject table 54 (the body axis direction of the subject H disposed on the subject table 54) is defined as a y-axis direction, a direction perpendicular to the y-axis direction in a radiographed surface (a surface irradiated with radiation) is defined as an x-axis direction, and a irradiation direction (the thickness direction of the subject H) is defined as a z-axis direction.

Components of the tomographic image generating system 100 are provided either inside or outside an imaging room 101A and a front room (a control room or another room) 101B. The tomographic image generating system 100 includes the radiographic imaging apparatus 1 having an imaging bed 50, a radiation source 61 and a three-dimensional camera 70 in the imaging room 101A. In the imaging room 101A, the tomographic image generating system 100 further includes an access point AP for relaying wireless communications between a radiation detector F and the console 90 described later.

In the front room 101B, the tomographic image generating system 100 includes an operator station 62 and an exposure switch 63 for an irradiation device 60. In FIG. 1, a control box 80, the console 90, and other devices are provided outside the front room 101B. These devices, however, may be provided inside the front room 101B or another room.

With reference to FIG. 1, the radiographic imaging apparatus 1, which serves as an imaging member, includes the radiation detector F, the imaging bed 50 for holding the radiation detector F and the subject H, and the irradiation device 60. FIG. 1 illustrates a side view of the radiographic imaging apparatus 1 imaging the subject H in a lying posture, for example.

The radiation detector F includes a flat panel detector (FPD) or any other semiconductor image sensor. For example, the FPD includes a glass substrate and a matrix of detecting elements (pixels) arrayed on a predetermined position of the glass substrate. The detecting elements detect radiation (x-rays), which is emitted from the radiation source 61 and at least passes through the subject H, in proportion to the intensity of the radiation, and convert the detected radiation into electrical signals and accumulate the electrical signals. Each pixel includes a switching section such as a thin film transistor (TFT). The radiographic imaging apparatus 1 reads electrical signals accumulated in the radiation detector F by switching the reading of electrical signals accumulated in the pixels with the switching sections such that the radiographic imaging apparatus 1 acquires projected images of the subject H. The FPD may be of an indirect type, which converts radiation into light by a scintillator and then converts the light into electrical signals by a photoelectric conversion element, or of a direct type, which directly converts radiation into electrical signals.

The value (the signal value) of each pixel of each projected image is the value of an electrical signal converted in proportion to the intensity of radiation incident on the radiation detector F, i.e. the value which correlates with the intensity of radiation incident on the radiation detector F. Thus, as the intensity of the incident radiation increases, the signal value increases. In this embodiment, as the signal value of the projected image increases, the blackness (the density) of the depicted image increases.

The radiation detector F has a function to communicate with the console 90 via a network N1 and the control box 80, and a function to wirelessly communicate with the console 90 via the access point AP.

The imaging bed 50 includes a detector loader 51, a loader support 52, a conveyor 53, and the subject table 54.

The detector loader 51 holds the radiation detector F.

The loader support 52 is provided on a surface of the subject table 54, which is opposite to the surface for placing the subject H. The loader support 52 supports the detector loader 51 and is movable in the longitudinal direction of the subject table 54 (the body axis direction of the subject H or Y-axis direction).

The conveyor 53 includes a drive motor (not shown), for example. The conveyor 53 transmits the turning force of the drive motor to the loader support 52 through rack-and-pinion gearing in order to move the loader support 52 in the longitudinal direction of the subject table 54 (y-axis direction). The conveyor 53 may have any unit and mechanism which can move the loader support 52 in the longitudinal direction of the subject table 54, other than the drive motor with rack-and-pinion gearing. For example, the conveyor 53 may include an actuator or another unit which transmits linear movement to the loader support 52 so as to move the loader support 52.

The subject table 54 supports the subject H so that the subject H is irradiated with radiation emitted from the radiation source 61. The subject table 54 is composed of an acrylic plate or any other resin plate, a carbon plate or any other plate of inorganic material, or a metallic plate. The subject table 54 includes guide rails (not shown) for moving the loader support 52 along the longitudinal direction of the subject table 54 (y-axis direction).

The irradiation device 60 includes the radiation source 61 for applying radiation to the radiation detector F through the subject H; the operator station 62 enabling a radiological technician or another radiographer to set imaging conditions such as tube current, tube voltage and irradiation time; the exposure switch 63 by which a radiographer can instruct to apply radiation from the radiation source 61; and a moving mechanism 64 both for moving the radiation source 61 along the body axis direction of the subject H on the subject table 54 (the y-axis direction) and for tilting the irradiating angle of the radiation source 61 depending on an moved position of the radiation source 61 such that the radiation detector F is irradiated with radiation applied from the radiation source 61 at the moved position. When a radiographer presses the exposure switch 63 after setting imaging conditions with the console 90 via the control box 80 or with the operator station 62, the irradiation device 60 sends a signal of the pressed exposure switch 63 to the console 90. Then, the irradiation device 60 causes the radiation source 61 to emit radiation while moving the radiation source 61 through the moving mechanism 64 according to control signals from the console 90 under the set imaging conditions.

The irradiation device 60 further includes a collimator 75, on an irradiation path of the radiation source 61, for defining an irradiation region of the radiation emitted from the radiation source 61.

In this embodiment, the radiation source 61 of the irradiation device 60 emits a cone beam of radiation conically toward the subject H and the radiation detector F. Alternatively, the radiation source 61 may emit a fan beam of radiation extending in a substantially plane like a fan from the radiation source 61. If the irradiation device 60 is equipped with a fan-beam radiation source, the radiation source applies radiation such that the width of the fan beam increases in the given direction as described above.

Figure 2:
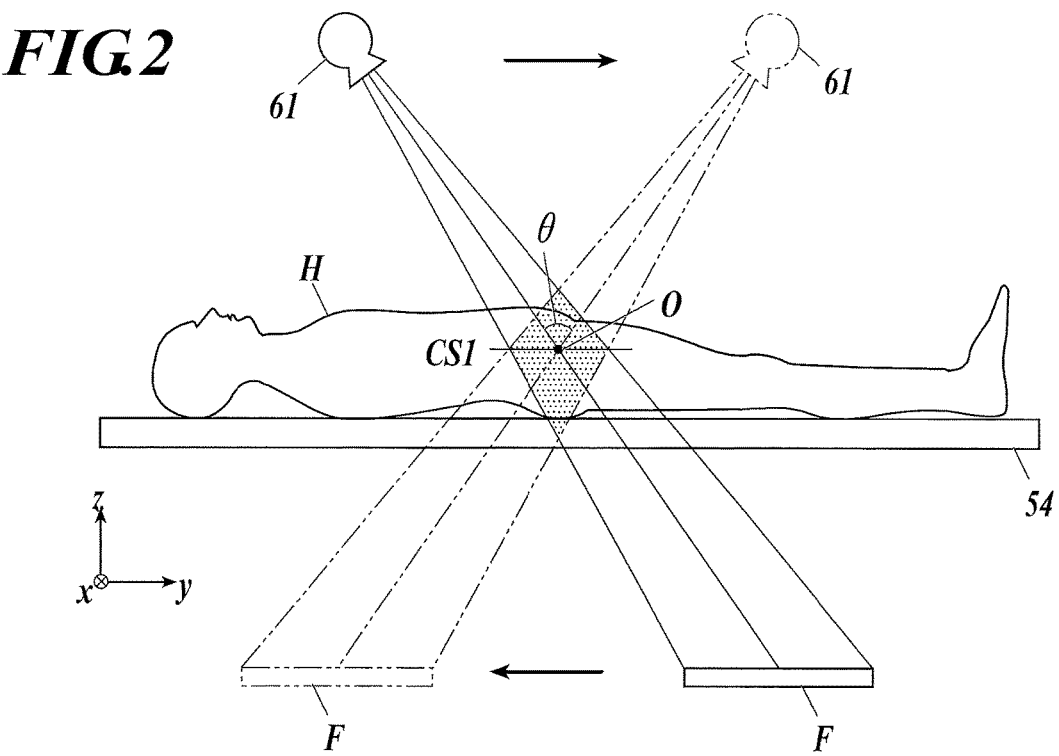
FIG. 2 is a diagram for explaining about tomosynthesis imaging, a swing angle of a radiation source, a center of rotation, etc.

The moving mechanism 64 and the conveyor 53 synchronize with each other in response to control signals sent from the console 90 via the control box 80 described later. The moving mechanism 64 and the conveyor 53 move the radiation source 61 and the loader support 52 symmetrically with respect to a rotation center O (refer to FIG. 2) along the subject table 54 (the y-axis) in mutually opposite directions so as to move the radiation source 61 and the radiation detector F in opposite directions, as shown in FIG. 2.

The radiographic imaging apparatus 1 described above performs tomosynthesis imaging a given number of times (more than once) so as to capture projected images on the radiation detector F every imaging while the radiation source 61 and the radiation detector F synchronously move from their respective predetermined start positions to end positions in opposite directions. During this operation, the optical axis of the radiation source 61 is projected toward the center of the radiation detector F.

The radiation detector F can acquire projected images a given number of times while the radiation source 61 is continuously applying radiation, for example. Alternatively, the radiation detector F may acquire projected images every time radiation are applied while the radiation source 61 applies radiation a given number of times (pulse irradiation).

Every time the radiation detector F acquires each projected image, the radiation detector F may transmit the projected image via the control box 80 to the console 90 acting as an image processing apparatus. Alternatively, the radiation detector F may temporarily store acquired projected images into a storage section (not shown) and transmit the projected images to the console 90 at the same time after the radiation detector F completes the acquisition of a given number of projected images.

The three-dimensional camera 70 is disposed in the vicinity of the radiation source 61 and is opposite to the surface of the subject table 54 on which the subject H is disposed. For example, the three-dimensional camera 70 includes a visible-light sensor(s) and an infrared sensor(s) arrayed two-dimensionally, which are opposite to the surface of the subject table 54 on which the subject H is disposed. The three-dimensional camera 70 functions as an acquiring member to radiograph the subject H in the irradiating direction of the radiation source 61, acquire a two-dimensional image (two-dimensional geometric image) and a distance image of the subject H, and output the images to the console 90. The distance image is an image representing a distribution of a distance from the three-dimensional camera 70 at individual positions in the imaging range of a two-dimensional image. Incidentally, though the three-dimensional camera 70 including the visible-light sensor(s) and infrared sensor(s) arrayed two-dimensionally is described above as an example, the three-dimensional camera 70 is not limited to this example as long as it can obtain two-dimensional images (two-dimensional shapes of subjects) and/or the distance images (thicknesses of subjects). For example, a laser scanner can be used.

The control box 80 (also called a repeater) is connected to each component of the radiographic imaging apparatus 1, the radiation detector F loaded on the detector loader 51, the console 90 and other devices via the network N1. The control box 80 has a built-in converter (not shown). The converter converts signals and other information for local area network (LAN) communications to signals and other information for the irradiation device 60, and vice versa. These signals are sent from the console 90 and other devices to the irradiation device 60.

Figure 3:
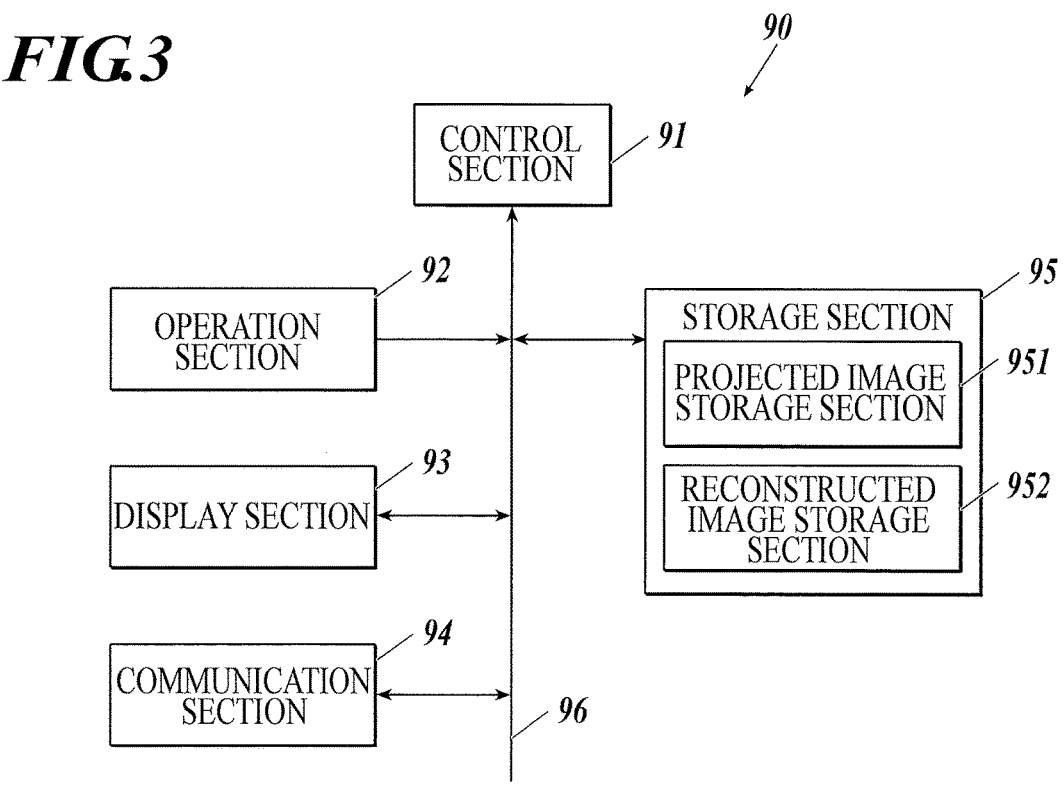
FIG. 3 is a functional block diagram of a console of FIG. 1.

With reference to FIG. 3, the console 90 is a computer apparatus including a control section 91, an operation section 92, a display section 93, a communication section 94, and a storage section 95. These sections are connected through a bus 96.

The control section 91 includes a CPU and a RAM. The CPU of the control section 91 reads various programs such as system programs and processing programs stored in the storage section 95 and loads them onto the RAM. Under instruction of the loaded programs, the CPU executes a reconstructed image generating process A and other processes described later. The control section 91 acts as a reconstructing member and a controlling member in cooperation with the programs stored in the storage section 95.

The operation section 92 includes a keyboard equipped with a text keypad, a numeric keypad and other function keys and a mouse or any other pointing device. The operation section 92 outputs signals generated through operation of the keyboard and the mouse, as input signals, to the control section 91.

The display section 93 includes a monitor such as a cathode ray tube (CRT) display and a liquid crystal display (LCD), for example. Under the instruction of display signals sent from the control section 91, the display section 93 displays various screens.

The communication section 94 includes a LAN card, and sends and receives data to and from the external devices connected to the network N1 and a network N2 via a switching hub.

The storage section 95 is composed of a hard disk drive (HDD) and nonvolatile semiconductor memory, for example. The storage section 95 stores the system programs and the various processing programs described above.

The storage section 95 includes a projected image storage section 951 for storing projected images received from the radiation detector F and a reconstructed image storage section 952 for storing generated reconstructed images.

The storage section 95 further stores patient information of accepted patients and other information.

The console 90 instructs the three-dimensional camera 70 to capture a two-dimensional image and a distance image of the subject H to acquire the thickness and/or the two-dimensional shape of the subject H, determines imaging conditions based on the acquired thickness and/or the two-dimensional shape of the subject H, and controls the irradiation device 60, the radiation detector F, and other components of the radiographic imaging apparatus 1 via the control box 80 according to the determined imaging conditions for tomosynthesis imaging. The two-dimensional shape of the subject refers to the profile of the boundary between the subject H and the other part on the surface irradiated with radiation (in the xy-plane).

In this embodiment, the console 90 also acts as an image processing apparatus. The console 90 determines reconstructing conditions based on the thickness and/or the two-dimensional shape of the subject H. When projected images captured on the radiation detector F are sent from the radiographic imaging apparatus 1, the console 90 reconstructs the projected images according to the determined reconstructing conditions so as to generate reconstructed images (two-dimensional tomographic images indicated by alternate long and short dashed lines in FIG. 1) of the subject H. Alternatively, the radiographic imaging apparatus may be an apparatus independent from the console 90.

With reference to FIG. 1, the console 90 is connected with the access point AP via the network N2. The console 90 is also connected with various systems (not shown) such as a Hospital Information System (HIS), a Radiology Information System (RIS), and a Picture Archiving and Communication System (PACS) via the network N2. The console 90 obtains imaging order information as to an imaging site of a patient who is an imaging target, an imaging direction, etc. from the HIS, the RIS and other systems, transmitting the generated reconstructed images to the PACS, and performs other operations.

In this embodiment, the separate networks N1 and N2 establish connections among the components/devices of the tomographic image generating system 100. Alternatively, the tomographic image generating system 100 may include a single network connecting these components/devices. If a tomographic image generating system includes two or more networks to connect components/devices like this embodiment, the components/devices can be independently connected to these networks as appropriate.

[Operation of Tomographic Image Generating System 100]

The operation of the tomographic image generating system 100 according to this embodiment will now be described.

In the tomographic image generating system 100, the control section 91 of the console 90 executes the reconstructed image generating process A described below. Through the process, the control section 91 controls each component of the radiographic imaging apparatus 1 to take a given number of radiographs while moving the radiation source 61 and the radiation detector F, and generates reconstructed images (tomographic images) by reconstructing the acquired series of projected images.

FIG. 4 illustrates a flowchart of the reconstructed image generating process A executed by the control section 91 of the console 90. The control section 91 executes the reconstructed image generating process A in cooperation with programs stored in the storage section 95.

The control section 91 firstly displays the patient stored in the storage section 95 on the display section 93, and acquires the patient information of a patient to be imaged, the order information as to an imaging site and an imaging direction, etc., on the basis of a selecting operation in the operation section 92 (Step S1). After selecting the patient information, the radiographer places the subject H (the site to be imaged) on the subject table 54 and performs positioning.

The control section 91 instructs the three-dimensional camera 70 to execute imaging so that at least a distance image in the imaging range including the subject H is obtained (Step S2).

The control section 91 acquires the thickness of the subject H based on the distance image captured with the three-dimensional camera 70 (Step S3). For example, the control section 91 measures the distance from the three-dimensional camera 70 to the subject table 54 in advance and stores it in the storage section 95. The control section 91 then calculates a differential value between the distance from the three-dimensional camera 70 to the subject table 54 and the distance from the three-dimensional camera 70 to each position (the x and y coordinates of each dot) in the imaging range. The control section 91 takes the differential value (more than zero) as the thickness of the subject H at each position and acquires a distribution of the thicknesses of the subject H (the thickness of the subject H at each position on the surface (xy-plane) irradiated with radiation).

The control section 91 determines imaging conditions based on the thickness of the subject H (Step S4).

The imaging conditions determined here include a swing angle θ of the radiation source 61, travel speeds and distances of the radiation source 61 and the radiation detector F, an irradiation field, the rotation center O, the number of times of imaging, the radiation integration time of the radiation detector F, irradiation time per projection, tube current, tube voltage, and an mAs value. In Step S4, at least one of these imaging conditions is determined.

With reference to FIG. 2, the swing angle θ is an angle at which the radiation source 61 moves during imaging with respect to the rotation center O detailed later (an angle formed by the imaging start and end positions of the radiation source 61 and the rotation center O).

As the swing angle θ increases, the volume of the information available for reconstruction increases and resolution increases across the thickness (depth) of the subject H. Nevertheless, if the swing angle θ is wider, the number of times of imaging inevitably increases and imaging takes more time. If the subject H has a structure inside, each reconstructed image of the subject H includes a false image (a ripple) corresponding to the structure in a direction parallel to the moving direction of the radiation source 61. The range in which the ripple extends is smaller at a narrower swing angle θ and is larger at a wider swing angle θ. The range in which the ripple extends is also larger at a larger distance to the radiation detector F. In other words, the thicker subject H is more susceptible to the ripple. Thus, if the subject H is thicker, the swing angle θ is set to be narrower. Specifically, the control section 91 acquires a typical value (e.g. the maximum value) from the distribution of the thicknesses of the subject H (the typical value is the maximum value in this example). If the typical value of the thickness of the subject H is larger, the swing angle θ is set to be narrower. The typical value of the thickness of the subject H represents an approximate thickness of the subject H and may be the median or the mean, other than the maximum value for example.

This configuration can automatically determine the optimal swing angle θ in proportion to the thickness of the subject H.

The travel speeds of the radiation source 61 and the radiation detector F refer to speeds at which the radiation source 61 and the radiation detector F travel from their respective imaging start positions to end positions during imaging.

A long imaging time increases the movement of the subject H. Thus, the imaging time is limited to be within a predetermined reference time. At an imaging time within the predetermined reference time, the travel speeds of the radiation source 61 and the radiation detector F depend on the swing angle θ determined by the thickness of the subject H and the reference time. In other words, this configuration can automatically determine the optimal travel speeds of the radiation source 61 and the radiation detector F in proportion to the thickness of the subject H.

The travel distances of the radiation source 61 and the radiation detector F depend on the swing angle θ determined by the thickness of the subject H. In other words, this configuration can automatically determine the optimal travel distances of the radiation source 61 and the radiation detector F in proportion to the thickness of the subject H.

The irradiation field is a range in which the radiation source 61 radiates radiation, and can be limited with the collimator 75. For example, the control section 91 defines an area in which the thickness of the subject is more than zero (i.e. an area where the subject H exists) as a subject area within the imaging range of the three-dimensional camera 70. The control section 91 determines an area, which is inside a rectangle circumscribing the subject area, to be an irradiation field. This configuration can automatically determine the optimal irradiation field without manual adjustment by the user.

With reference to FIG. 2, the rotation center O is a reference point to which the radiation source 61 and the radiation detector F symmetrically move during imaging.

Radiography at multiple exposure points accompanied with movement of the radiation source 61 and the radiation detector F from the positions indicated with real lines to the positions indicated with dot-and-dash lines in FIG. 2 defines a space irradiated with radiation at all the exposure points, as shown by dots in FIG. 2, for example. Specifically, the space irradiated with radiation at all the exposure points has the largest horizontal area in a cross section CS1 containing the rotation center O. That horizontal area decreases with an increase in distance from the rotation center O. At sites irradiated with no radiation among all the exposure points, images appear blurred because imaging without radiation gives no information.

Thus, the control section 91 determines the position of the rotation center O such that the cross section at the middle of the subject H across the thickness contains the rotation center O (e.g. the cross section at a depth corresponding to the middle of the typical value of the thickness of the subject H). This maximizes the space irradiated with radiation at all the exposure points (the space indicated with dots of FIG. 2) in the subject H. In other words, this configuration can automatically determine the optimal position of the rotation center O in proportion to the thickness of the subject H.

the number of times of imaging refers to the number of times the radiographic imaging apparatus 1 repeats radiography while the radiation source 61 and the radiation detector F are traveling from their respective imaging start positions to end positions during imaging. Since the number of times of imaging should increase as the swing angle θ increases, the number of times of imaging depends on the swing angle θ determined by the thickness of the subject H. This configuration can automatically determine the optimal number of times of imaging in proportion to the thickness of the subject H.

The radiation integration time of the radiation detector F refers to the time during which the radiation detector F accumulates radiation to generate projected images. The dose of radiation incident on the radiation detector F decreases as the subject H gets thicker. Thus, the radiation integration time of the radiation detector F is set to a larger value as the thickness of the subject H (e.g. the typical value of the thickness of the subject H) increases. This configuration can automatically determine the optimal radiation integration time for the radiation detector F in proportion to the thickness of the subject H.

The dose of radiation incident on the radiation detector F decreases as the subject H gets thicker. Thus, the tube voltage, the tube current, the irradiation time per projection, and the mAs value are set to larger values as the thickness of the subject H (e.g. the typical value of the thickness of the subject H) increases.

The imaging conditions other than the irradiation field may be determined in reference to a table of the correspondence between the typical value (the maximum value) of the thickness of the subject and each imaging condition, which is stored in the storage section 95 in advance. The control section 91 refers this table in Step S4. Alternatively, the imaging conditions may be determined by computation as occasion demands.

The control section 91 performs the tomosynthesis imaging under the determined imaging conditions (Step S5).

The control section 91 controls each component of the radiographic imaging apparatus 1 through the control box 80 so as to cause the apparatus 1 to take a given number of radiographs accompanied with the movement of the radiation source 61 and the radiation detector F symmetrically about the rotation center O along the body axis direction of the subject H in mutually opposite directions. The radiation detector F sends a series of projected images acquired through the imaging to the console 90. The console 90 stores the series of projected images received at the communication section 94 into the projected image storage section 951.

Then, the control section 91 determines the reconstructing conditions based on the thickness of the subject H (Step S6).

The reconstructing conditions determined here include the reconstruction range of the subject H, in-plane resolution, a slice pitch, parameters for determining tomographic slice thickness, and the number of iterations in the Iterative Reconstruction. In Step S6, at least one of these reconstructing conditions is determined.

The reconstruction range of the subject H refers to a range for generating reconstructed images (a range where calculation is made for reconstruction).

If a reconstructable range in the thickness direction (z-axis direction) of the subject H is a range shown with the grid pattern of FIG. 5A, the control section 91 removes an area containing no subject H (as shown by dots in FIG. 5A) in the reconstructable range, from the reconstruction range, on the basis of the distribution of the thicknesses of the subject H. Alternatively, the reconstruction range in the thickness direction of the subject H may be defined so as to contain up to the typical value (the maximum value) of the thickness of the subject H. If the reconstructable range in the surface (xy-plane) of the subject H irradiated with radiation is a range shown by the grid pattern in FIG. 5B, the control section 91 specifies an area containing the subject H (e.g. an area where the thickness of the subject H is more than zero) based on the distribution of the thicknesses of the subject H, and removes the rest of the range containing no subject H (as shown by dots in FIG. 5B) from the reconstruction range. This configuration can automatically determine the optimal reconstruction range, reducing the processing time for image reconstruction. This configuration also eliminates complicated calculation of redundant areas, improving processing accuracy.

The in-plane resolution refers to the pixel pitch of each reconstructed image. The reconstruction range of the subject H in the xy-plane is obtained based on the distribution of the thicknesses of the subject H as described above. If the reconstruction range is small, the processing does not take much time even with a small pixel pitch. Thus, the pixel pitch is set to a small value (i.e. high in-plane resolution). If the reconstruction range is large, a small pixel pitch results in much processing time. Thus, the pixel pitch is set to a large value (i.e. low in-plane resolution). In other words, the in-plane resolution is determined based on the distribution of the thicknesses of the subject H. This configuration can automatically determine the optimal in-plane resolution according to the distribution of the thicknesses of the subject H.

The slice pitch refers to a spacing between tomographic cross-sections (shown by TH in FIG. 1) in generating reconstructed images. If an identical slice pitch is applied to two subjects H with different thicknesses, calculation takes more time as the thickness of the subject H increases. Thus, the slice pitch is determined depending on the thickness (e.g. the typical value) of the subject H. Specifically, the slice pitch is set to a greater value at a larger thickness of the subject H, such that the calculation time for generating reconstructed images is kept constant. This also narrows the range of calculation for reconstruction, improving accuracy in calculation.

Figure 6A:
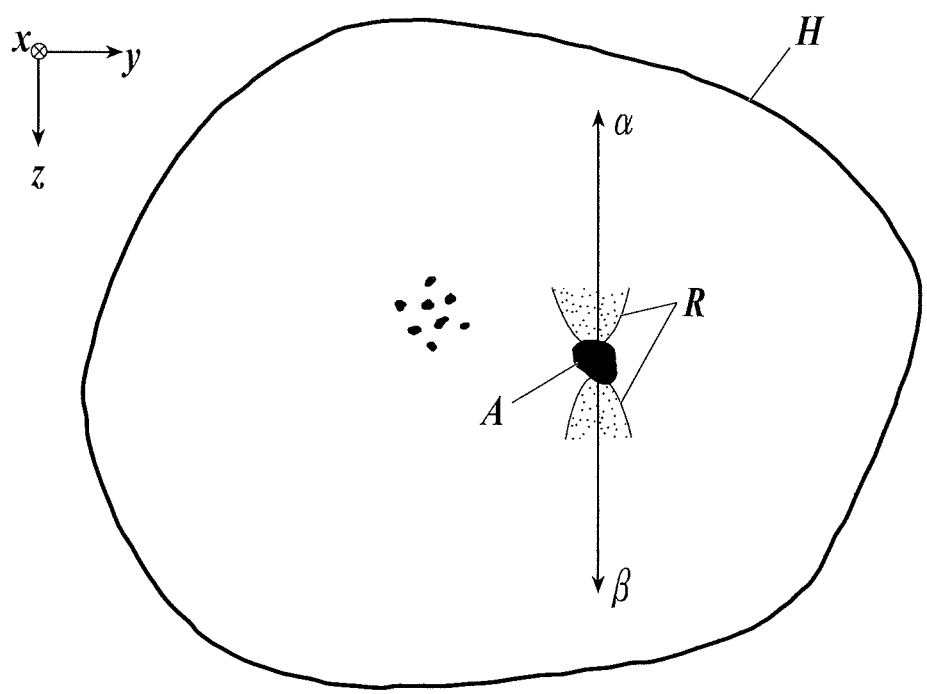
FIG. 6A is a diagram illustrating blurring R of a subject in the thickness direction.
Figure 6B:
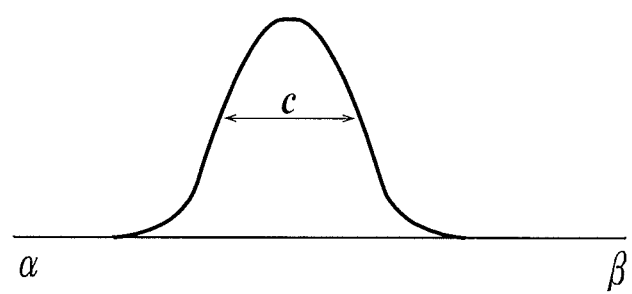
FIG. 6B is a diagram illustrating a signal value profile $\alpha$-$\beta$ on the blurring R of FIG. 6A in the thickness direction and a half-value width of the signal value profile $\alpha$-$\beta$.

The tomographic slice thickness represents the extent of blurring of each reconstructed image across the thickness. If the subject H includes a structure A as shown in FIG. 6A and if a signal value profile α-β on blurring R of the reconstructed image of the subject H is taken in the thickness direction, the tomographic slice thickness is determined using a half-value width C of that profile, as shown in FIG. 6B. The tomographic slice thickness can be varied by image processing. For example, the tomographic slice thickness can be varied by overlapping multiple cross-sectional images and averaging them in generation of a single reconstructed image. Parameters for determining tomographic slice thickness include the number of these images to be averaged and the shape of a reconstruction filter.

If the slice pitch is large, it is preferred that the tomographic slice thickness be large so as to prevent the oversight of a lesion between slices (reconstructed images). As described above, the slice pitch is determined depends on the thickness of the subject H. Thus, parameters for determining the tomographic slice thickness are also set according to the thickness of the subject H, for example, such that the tomographic slice thickness increases with the thickness of the subject H. This configuration can automatically determine the optimal tomographic slice thickness based on the thickness of the subject H.

The number of iterations in the Iterative Reconstruction refers to the number of iterations for updating reconstructed images in the Iterative Reconstruction to be described later.

The process of generating reconstructed images takes a longer processing time as the number of slices and the number of iterations increase. The number of slices is calculated from the reconstruction range and the slice pitch determined by the thickness of the subject H using the expression (the number of slices=reconstruction range of subject H in thickness direction/slice pitch+1). Thus, the number of iterations is limited to a smaller value as the number of slices increases such that the processing time is limited to within a predetermined time period. In other words, the number of iterations in the Iterative Reconstruction is determined based on the thickness of the subject H. This configuration can automatically determine the optimal number of iterations in the Iterative Reconstruction in proportion to the thickness of the subject H.

The reconstructing conditions other than the reconstruction range and the in-plane resolution may be determined in reference to a table of the correspondence between the typical value (the maximum value) of the thickness of the subject and each reconstructing condition, which is stored in the storage section 95 in advance. The control section 91 refers to this table to determine the reconstructing conditions in Step S6. Alternatively, the reconstructing conditions may be determined by computation as occasion demands.

The control section 91 generates reconstructed images (tomographic images) of the subject H based on the projected images stored in the projected image storage section 951, and stores them in connection with the patient information in the reconstructed image storage section 952 (Step S7). Examples of methods for image reconstruction include the Iterative Reconstruction, a filtered back projection (FBP) method, a Feldkamp method, a shift-and-add method, and any other publicly known method.

The Iterative Reconstruction will now be described as a typical example of the image reconstruction.

The Iterative Reconstruction is publicly known as described in Reference 1 (Gazo Saikosei Series Chikuji Kinji Gazo Saikosei no Kiso=Image Reconstruction Series: Fundamental Iterative Reconstruction, by Hiroyuki Shinohara, Kazuma Nakazeko, Kazuya Sakaguchi, and Takeyuki Hashimoto, published by Iryo Kagaku-sya, 2013). The Iterative Reconstruction generally involves building a model, for example, an optical model (e.g. a detection probability), a statistical model, or any other model, projecting a certain supposed reconstructed image, on a computer, using the model to create a projected image(s) (referred to as an estimated projected image(s)), comparing the estimated projected image with each projected image actually radiographed, obtaining a feedback value through the back projection of the results of the comparison, and iteratively updating the reconstructed image with the feedback value so as to make the reconstructed image closer to the real reconstructed image. Examples of the Iterative Reconstruction using detection probability include a Simultaneous Iterative Reconstruction Technique (SIRT) and a Maximum Likelihood-Expectation Maximization (ML-EM) algorithm. The SIRT (multiplication type) will now be described as an example. In the following description, the pixel and the detector are denoted as one-dimensional variables, and parameters for determining the thickness of the tomographic slice are the number of multiple cross-sectional images to be averaged.

Figure 7:
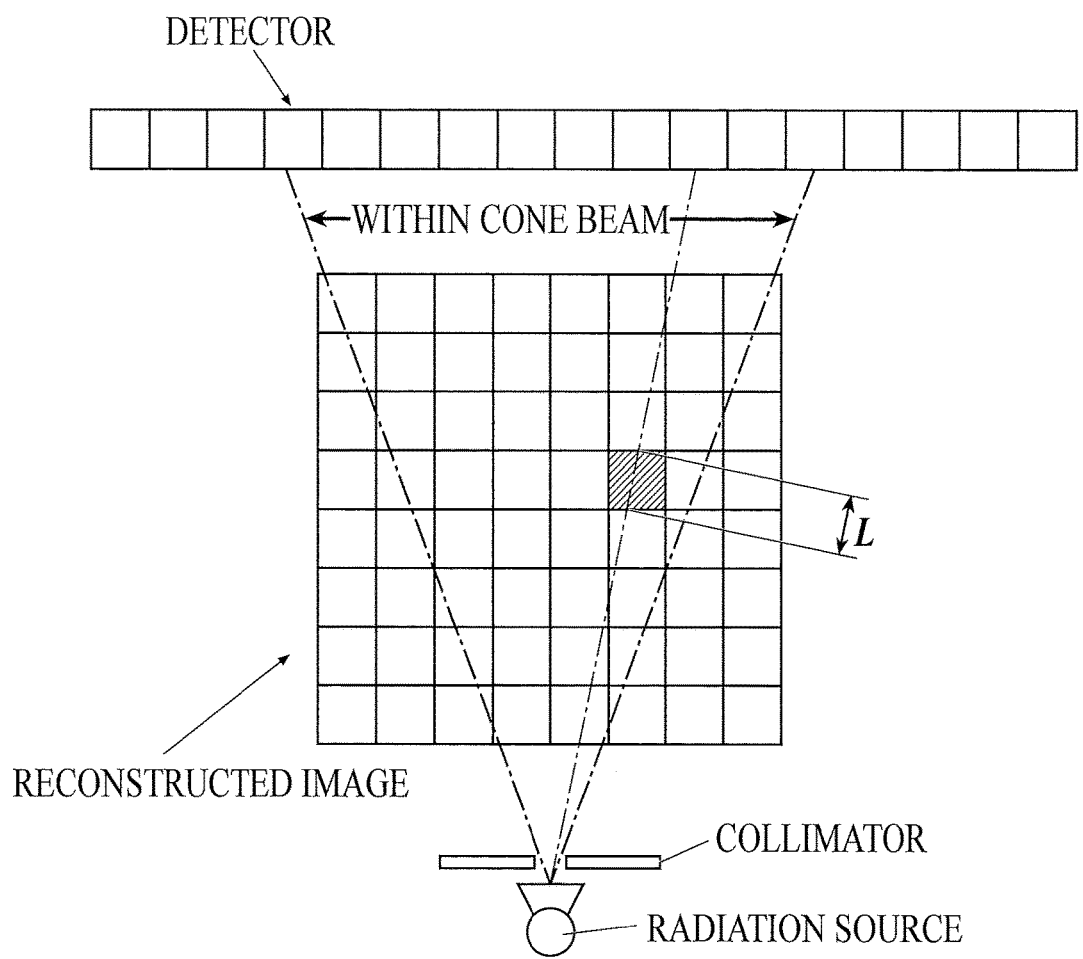
FIG. 7 is a diagram for explaining about example calculation of a detection probability in Iterative Reconstruction.

In the Iterative Reconstruction, the detection probability Cij is a probability indicating the effect of the j_th pixel (a pixel j) in a reconstructed image on the i_th detector (a detector i; detecting element). The detection probability Cij is determined by a geometrical arrangement of the pixel j and the detector i. The "j" is a number assigned to a pixel at the x and y coordinates on a reconstructed image, whereas the "i" is a number assigned to the pixel of the detector at a coordinate (s,θ0) representing the position s and the projection angle θ0. The detection probability Cij can include blurred focus, photon scattering, and other physical phenomena. Various methods for calculating the detection probability Cij have been proposed. With reference to FIG. 7, if the projection line of radiation (shown by thin dot-and-dash lines in FIG. 7) connects the focus of the radiation source with the center of the detector while actual projected images in different directions are collected for a reconstructed image, the detection probability Cij is determined by the length of a line segment L, over which the projection line connecting the focus of the radiation source with the center of the detector i crosses the pixel j, for example. Alternatively, the detection probability Cij may equal the area of the intersection of the projection line having a width of one pixel and the pixel j. The detection probability Cij may be calculated for every combination of the pixels and the detectors in advance, or may be calculated as occasion demands.

In the SIRT (multiplication type), the k+1_th reconstructed image is created based on the k_th reconstructed image using the detection probability Cij in the following steps (1) to (4), where "k" represents the update number; "j" represents the pixel number of reconstructed image; "J" represents the total number of pixels; "i" represents the number assigned to the detector (detecting element); "I" represents the total number of detectors; "Cij" represents the detection probability; λj(k) and λj(k+1) represent pixel values of the k_th and the k+1_th created reconstructed images, respectively; and "yi" represents the value of the projected image actually radiographed (actual projected image).

(1) The k-th estimated projected image yi(k) is calculated from Expression 1 including the detection probability Cij where the k_th reconstructed image λj(k) is projected to estimate the k-th projected image yi(k)):

$$y_i^k = \sum_{m=1}^{J} C_{im} \lambda_m^k \qquad \text{[Expression 1]}$$

(2) The ratio yi' of the actual projected image yi to the k-th estimated projected image yi(k) is calculated from Expression 2:

$$y'_i = \frac{y_i}{y_i^k} \quad \text{[Expression 2]}$$

(3) The feedback value λj' is calculated from Expression 3 including the detection probability Cij where the calculated ratio yi' is back-projected:

$$\lambda'_j = \frac{1}{\sum_{i=1}^{I} C_{ij}} \sum_{i=1}^{I} y'_i C_{ij} \quad \text{[Expression 3]}$$

(4) The k+1_th reconstructed image λj(k+1) is calculated from Expression 4, where the k_th reconstructed image λj(k) is multiplied by the feedback value λj':

$$\lambda_j^{k+1} = \lambda_j^k \cdot \lambda'_j \quad \text{[Expression 4]}$$

Steps (1) to (4) are repeated to satisfy a given condition, for example, until the number of updates reaches a predetermined number or the difference between the estimated projected image yi(k) and the actual projected image yi falls below a predetermined threshold. The number of times repeated here is equal to the number of iterations described above. It is also possible to average plural reconstructed images, which are adjacent to one another in a direction perpendicular to the tomographic cross-sections, to change the tomographic slice thickness. For example, if the slice pitch is constant, the larger the number of images to be averaged, the larger the tomographic slice thickness. The final reconstructed images are thus created. This process is repeated over the number of slices at the determined slice pitch.

Information on the thickness distribution of the subject H can be used as a priori information, as well as for determining the reconstructing conditions. For example, pixels containing no subject H is specified in the reconstruction range on the basis of the thickness distribution of the subject H and a predetermined value (for example 0) is preliminarily assigned to each of the specified pixels in the reconstruction range to define the pixel as one having a known value. This can simplify calculation in the creation of reconstructed images, leading to improved calculation accuracy and a shortened process time.

The information on the thickness distribution of the subject H can also be used to increase the accuracy of the detection probability Cij.

Figure 8A:
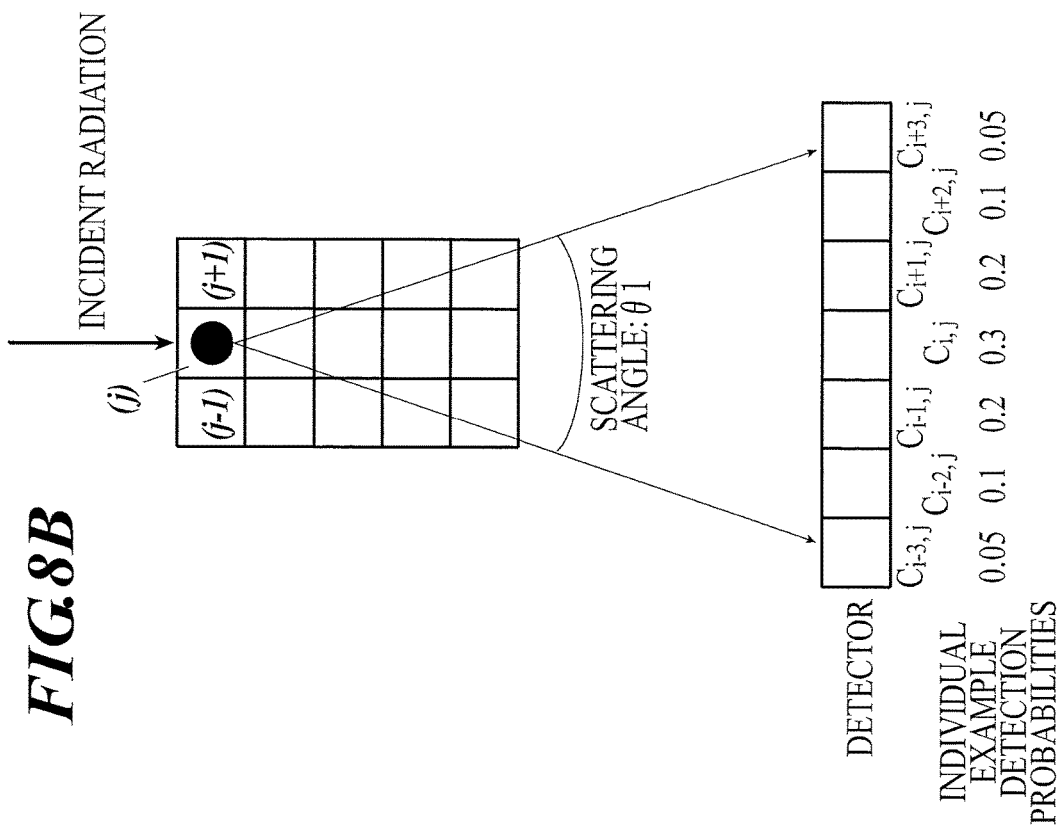
FIG. 8A is a diagram illustrating example detection probabilities $C(i-3, j)$ to $C(i+3, j)$ for a thin subject in consideration of an effect of scattered radiation.
Figure 8B:
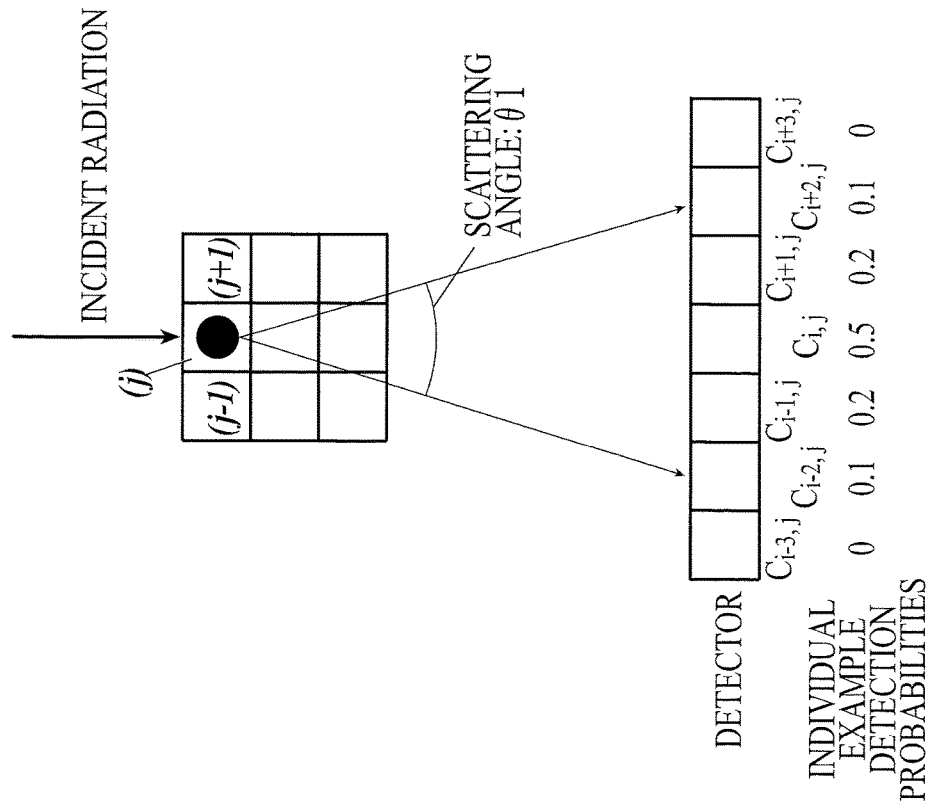
FIG. 8B is a diagram illustrating example detection probabilities $C(i-3, j)$ to $C(i+3, j)$ for a thick subject in consideration of the effect of the scattered radiation.

FIG. 8A illustrates example detection probabilities C(i−3, j) to C(i+3, j) for a thin subject in consideration of the effect of scattered radiation, whereas FIG. 8B illustrates example detection probabilities C(i−3, j) to C(i+3, j) for a thick subject in consideration of the effect of scattered radiation.

Although the detection probability Cij is described out of consideration of scattered radiation, scattered radiation is actually generated when radiation incident on the subject H pass through the structure, as shown in FIGS. 8A and 8B. With reference to FIG. 8B, the area on the radiation detector F scattered radiation reaches (the area influenced by scattered radiation) increases as the thickness of the subject H increases, even if both scattering angles θ1 are identical. Thus, the control section 91 determines the detection probability Cij on the basis of the thickness of the subject H. In the case of a thin subject H in FIG. 8A, the control section 91 determines the detection probabilities C(i−3, j) and C(i+3, j) to be zero since the detectors i−3 and i+3 are not influenced by incident radiation and scattered radiation, for example. In the case of a thick subject H in FIG. 8B, the control section 91 determines the detection probabilities C(i−3, j) and C(i+3, j) to be a value (e.g. 0.05) in consideration of the effect of the scattered radiation because the detectors i−3 and i+3 are influenced by scattered radiation.

In this embodiment, the control section 91 determines the detection probability Cij on the basis of the thickness of the subject H, and thus increases the accuracy of the detection probability Cij. Such high accuracy can also improve the accuracy of reconstructed images generated thereby.

In the embodiment described above, the imaging and the reconstructing conditions are determined on the basis of the thickness distribution of the subject H captured through the three-dimensional camera 70 (or the typical value acquired from the thickness distribution of the subject H). Alternatively, the imaging and the reconstructing conditions may be determined on the basis of a typical value of the thickness of the subject H, which is acquired by measuring the thickness of the thickest position (a point or a line) of the subject H using a distance sensor or any other measuring instrument, for example. In this case, the imaging and the reconstructing conditions, which are determined depending on the typical value of the thickness of the subject H in the embodiment described above, can be determined. Specifically, at least one imaging condition is determined of the mAs value, tube current, tube voltage, swing angle θ, travel speeds and distances of the radiation source 61 and the radiation detector F, rotation center O, the number of times of imaging, the radiation integration time of the radiation detector F, and irradiation time per projection, and at least one reconstructing condition is determined of the reconstruction range of the subject H in the thickness direction, slice pitch, parameters for determining the tomographic slice thickness, and the number of iterations in the Iterative Reconstruction. The detection probability Cij in the Iterative Reconstruction may also be determined on the basis of the typical value of the thickness of the subject H.

As described above, the tomographic image generating system 100 according to the first embodiment acquires the thickness of the subject H and automatically determines the imaging and the reconstructing conditions according to the acquired thickness of the subject H. Thus, the tomographic image generating system 100 can determine the optimal imaging and reconstructing conditions on the basis of the thickness of a subject H, reducing the workload of radiographers.

Second Embodiment

A second embodiment of the present invention will now be described.

In the first embodiment described above, the imaging and the reconstructing conditions are calculated on the basis of the distance image captured with the three-dimensional camera 70. A tomographic image generating system 100 according to the second embodiment determines imaging and reconstructing conditions on the basis of a two-dimensional image captured with a three-dimensional camera 70.

Since the first and the second embodiments have similar configurations, redundant descriptions on the configuration are omitted. Only the operation of the tomographic image generating system 100 according to the second embodiment will be described.

FIG. 9 illustrates a flowchart of a reconstructed image generating process B executed by a control section 91 according to the second embodiment. The control section 91 executes the reconstructed image generating process B in cooperation with programs stored in a storage section 95.

The control section 91 displays the patient information stored in the storage section 95 on a display section 93, and acquires the patient information on a patient who is an imaging target and the order information including the imaging site and imaging direction, on the basis of the selection operation in the operation section 92 (Step S11).

The control section 91 then instructs the three-dimensional camera 70 to take an image to acquire at least a two-dimensional image of a subject H in the imaging range (Step S12).

Next, the control section 91 acquires a two-dimensional shape of the subject H based on the two-dimensional image captured with the three-dimensional camera 70 (Step S13). For example, the control section 91 detects edge of the two-dimensional image to acquire the two-dimensional shape of the subject H, from the two-dimensional image, based on edge information and/or color information. Any method other than edge detection may also be used to acquire the two-dimensional shape of the subject H from the two-dimensional image.

The control section 91 determines an imaging condition based on the two-dimensional shape of the subject H (Step S14).

The imaging condition determined here is an irradiation field, for example.

The control section 91 defines a rectangle circumscribing the subject H based on the two-dimensional shape of the subject H and determines an area inside the rectangle to be an irradiation field, for example. This configuration can automatically determine the optimal irradiation field without manual adjustment by the user.

The other imaging conditions may be automatically determined on the basis of the distance image, as described in the first embodiment, or may be manually set by a radiological technician or another radiographer through an operator station 62.

The control section 91 then performs tomosynthesis imaging under the determined imaging conditions (Step S15). Since processing in Step S15 is similar to that in Step S5, redundant descriptions on that are omitted.

Next, the control section 91 determines reconstructing conditions based on the two-dimensional shape of the subject H (Step S16).

The reconstructing conditions determined here include a reconstruction range in the surface (xy-plane) of the subject H irradiated with radiation, in-plane resolution, and the number of iterations in the Iterative Reconstruction. In Step S16, at least one of these reconstructing conditions is determined.

For example, if the reconstructable range in the tomographic cross-section of the subject H is a range shown by the grid pattern in FIG. 5B, the control section 91 defines a rectangle circumscribing the edge of the subject H based on the two-dimensional shape of the subject H, and removes, from the reconstruction range, areas outside the rectangle (as shown by dots in FIG. 5B) in the reconstructable range. This configuration can automatically determine the optimal reconstruction range, reducing the processing time for image reconstruction. This configuration also eliminates complicated calculation of redundant areas, improving the processing accuracy.

The reconstruction range of the subject H in the xy-plane is obtained based on the two-dimensional shape of the subject H as described above. If a narrow reconstruction range is determined by the two-dimensional shape of the subject H, the process does not take much time even at a small pixel pitch. Thus, the pixel pitch is set to a small value (i.e. high in-plane resolution). If a wide reconstruction range is determined by the two-dimensional shape of the subject H, a small pixel pitch results in much processing time. Thus, the pixel pitch is set to a large value (i.e. low in-plane resolution). In other words, the in-plane resolution is determined based on the two-dimensional shape of the subject H. This configuration can automatically determine the optimal in-plane resolution on the basis of the two-dimensional shape of the subject H.

The process of image reconstruction takes more time as the reconstruction range increases. Thus, the number of iterations in the Iterative Reconstruction is limited to a smaller value as the reconstruction range determined by the two-dimensional shape of the subject H increases, such that the processing time is limited to within a predetermined time period. In other words, the number of iterations in the Iterative Reconstruction is determined based on the two-dimensional shape of the subject H. This configuration can automatically determine the optimal number of iterations on the basis of the two-dimensional shape of the subject H.

The other reconstructing conditions may be automatically determined on the basis of the distance image, as described in the first embodiment, or may be manually set by a radiological technician or another radiographer through the operator station 62.

The information on the two-dimensional shape of the subject H can be used as a priori information, as well as for determining the reconstructing conditions. For example, pixels containing no subject H may be specified in the reconstruction range on the basis of the two-dimensional shape of the subject H and a predetermined value (e.g. zero) is preliminarily assigned to each of the specified pixels in the reconstruction range to define the pixel as one having a known value. This can simplify calculation in the creation of reconstructed images, leading to improved calculation accuracy and a shortened processing time.

The control section 91 generates reconstructed images (tomographic images) of the subject H based on projected images stored in the projected image storage section 951 (Step S17). Since processing in Step S17 is similar to that in Step S7, redundant descriptions on that are omitted.

As described above, the tomographic image generating system 100 according to the second embodiment acquires the two-dimensional shape of the subject H and automatically determines the imaging and the reconstructing conditions based on the acquired two-dimensional shape of the subject H. Thus, the tomographic image generating system 100 can determine optimal imaging and reconstructing conditions on the basis of the two-dimensional shape of the subject H, reducing the workload of radiographers.

Third Embodiment

A third embodiment of the present invention will now be described.

A tomographic image generating system 100 according to the third embodiment recognizes the site of the subject H on the basis of a two-dimensional image captured with a three-dimensional camera 70 and calculates imaging and reconstructing conditions on the basis of the recognized site.

Since the first and the third embodiments have similar configurations, redundant descriptions on the configuration are omitted. Only the operation of the tomographic image generating system 100 according to the third embodiment will be described.

FIG. 10 illustrates a flowchart of a reconstructed image generating process C executed by a control section 91 according to the third embodiment. The control section 91 executes the reconstructed image generating process C in cooperation with programs stored in a storage section 95.

First, the control section 91 displays the patient information stored in the storage section 95 on a display section 93, and acquires the patient information on a patient who is an imaging target and the order information including an imaging site and an imaging direction, on the basis of the selection operation in the operation section 92 (Step S21).

The control section 91 then instructs the three-dimensional camera 70 to take an image to acquire at least a two-dimensional image of the subject H in the imaging range (Step S22). The two-dimensional image containing the subject H allows the control section 91 to acquire the two-dimensional shape of the subject H.

Next, the control section 91 analyzes the acquired two-dimensional image to recognize the site of the subject H (Step S23). For example, the control section 91 preliminarily stores template images of individual sites in the storage section 95, and recognizes a site of a template image having the highest similarity to the two-dimensional image acquired in Step S22 as the site of the subject H. Instead, any method for specifying the site may be used, other than the example given here. The control section 91 may retrieve information on sites to be radiographed from the RIS and other systems. In this case, the control section 91 may issue a warning if the specified result differs from the retrieved information.

Then, the control section 91 determines imaging conditions based on the recognized site of the subject H (Step S24).

The imaging conditions determined in this step include the swing angle θ of a radiation source 61, the travel speeds and distances of the radiation source 61 and a radiation detector F, the number of times of imaging, the Source Image receptor Distance (SID), the radiation integration time of the radiation detector F, the irradiation time per projection, binning size, the mAs value, the tube current, and the tube voltage. In Step S24, at least one of these imaging conditions is determined.

As the swing angle θ increases, the volume of the information available for reconstruction increases and resolution increases across the thickness (depth) of the subject H, as described above. Resolution required across the thickness depends on the site. Thus, the swing angle θ is determined based on the recognized site. This configuration can automatically determine the optimal swing angle θ on the basis of the site of the subject H.

If the imaging time is limited within the predetermined reference time as described above, the travel speeds of the radiation source 61 and the radiation detector F are determined based on the swing angle θ determined by the site of the subject H and the reference time. Thus, the travel speeds of the radiation source 61 and the radiation detector F are determined based on the site of the subject H. This configuration can automatically determine the optimal travel speeds of the radiation source 61 and the radiation detector F on the basis of the site of the subject H.

The travel distances of the radiation source 61 and the radiation detector F are determined based on the swing angle θ determined by the site of the subject H. In other words, this configuration can automatically determine the optimal travel distances of the radiation source 61 and the radiation detector F on the basis of the site of the subject H.

As described above, the appropriate number of times of imaging varies with the site. This configuration can automatically determine the optimal number of times of imaging on the basis of the site of the subject H.

As described above, the dose of radiation incident on the radiation detector F varies with the thickness of the subject H. Thus, the radiation integration time of the radiation detector F should be determined depending on the dose of radiation incident on the radiation detector F. The thickness of the subject H is partly determined by the site. Thus, the radiation integration time of the radiation detector F is determined based on the site of the subject H. This configuration can automatically determine the optimal radiation integration time for the radiation detector F on the basis of the site of the subject H.

The binning size refers to the size of a block of multiple pixels corresponding to multiple detecting elements on the radiation detector F, wherein the block of the pixels is regarded as a single pixel. As the binning size increases, the number of pixels for processing decreases. An image with a large binning size, however, does not satisfy the need for observation of a detailed structure. The need to observe a detailed structure depends on the site. Thus, the binning size is determined by the site of the subject H. This configuration can automatically determine the optimal binning size on the basis of the site of the subject H.

The Source Image receptor Distance (SID) refers to a distance between the radiation source 61 and the radiation detector F. Each site has an appropriate SID. Thus, the SID is determined based on the recognized site. This configuration can automatically determine the optimal SID on the basis of the site of the subject H.

As described above, the dose of radiation incident on the radiation detector F varies with the thickness of the subject H. Thus, the tube voltage, the tube current, the irradiation time per projection, and the mAs value are determined according to the site of the subject H such that radiation with a constant dose are incident on the radiation detector F.

The storage section 95 preliminarily stores a table of the correspondence between the site of the subject H and each imaging condition described above. The control section 91 determines the imaging conditions in reference to this table in Step S24.

The control section 91 performs the tomosynthesis imaging under the determined imaging conditions (Step S25). Since processing in Step S25 is similar to that in Step S5, redundant descriptions on that are omitted.

The control section 91 determines reconstructing conditions based on the recognized site of the subject H (Step S26).

The reconstructing conditions determined in this step include the in-plane resolution, slice pitch, parameters for determining tomographic slice thickness, parameters for determining sharpness and granularity in an FBP method, and number of iterations in the Iterative Reconstruction. In Step S26, at least one of these reconstructing conditions is determined.

The resolution (in-plane resolution) of the image, the slice pitch, and the tomographic slice thickness required for diagnoses depend on the site of the subject H. Thus, the in-plane resolution, the slice pitch, and parameters for determining the tomographic slice thickness are determined depending on the site of the subject H. This configuration automatically determine the optimal in-plane resolution, slice pitch and parameters for determining the tomographic slice thickness on the basis of the site of the subject H.

As the number of iterations in the Iterative Reconstruction increases, the clearness of the reconstructed images increases. The process of image reconstruction, however, takes a longer processing time as the number of iterations increases. Thus, the control section 91 determines the number of iterations depending on the site. For example, a larger number of iterations is assigned to sites which require more clearness in the image, whereas a smaller number of iterations is assigned to sites which does not require such clearness. This configuration can automatically determine the optimal number of iterations on the basis of the site of the subject H.

The sharpness and the granularity of the reconstructed images required for diagnoses depend on the site of the subject H. The FBP method, a typical image reconstruction method, involves the Fourier transformation of projected images, filtering of the projected images in the frequency domain, the inverse Fourier transformation of the filtered projected images, and accumulation of all the resulting projected images per pixel. The sharpness and the granularity of the reconstructed images can be varied by changing the shape of the filter that is used for filtering in the frequency domain. Thus, if reconstruction imaging is performed by the FBP method, the control section 91 determines the shape of the filter used in the frequency domain on the basis of the site of the subject H. This configuration can automatically set parameters for determining the optimal sharpness and granularity on the basis of the site of the subject H. Alternatively, projected images may be filtered by performing convolution of a filter factor with the projected images in a real spatial domain, other than filtering in the frequency domain as described above.

The storage section 95 preliminarily stores a table of the correspondence between the site of the subject H and each reconstructing condition. The control section 91 determines the reconstructing conditions in reference to this table in Step S26.

Next, the control section 91 generates the reconstructed images (tomographic images) of the subject H based on the projected images stored in the projected image storage section 951 (Step S27). Since processing in Step S27 is similar to that in Step S7, redundant descriptions on that are omitted.

As described above, the tomographic image generating system 100 according to the third embodiment acquires a two-dimensional shape of the subject H, recognizes the site of the subject H on the basis of the acquired two-dimensional shape, and automatically determines the imaging and the reconstructing conditions based on the recognized site of the subject H. Thus, the tomographic image generating system 100 can determine the optimal imaging and reconstructing conditions on the basis of the site of the subject H, reducing the workload of radiographers.

<Variation>

In the third embodiment described above, the tomographic image generating system 100 recognizes the site of the subject H by analyzing the two-dimensional image acquired with the three-dimensional camera 70 in Step S23. The tomographic image generating system 100 may also recognize the imaging direction of the subject H (the front view or either side view). For example, the tomographic image generating system 100 may perform facial recognition on the two-dimensional image and determine the recognized face to be the front view or side view so as to recognize the imaging direction. Incidentally, for example, the tomographic image generating system 100 may retrieve information on imaging directions from the RIS or any other system. In this case, the tomographic image generating system 100 may issue a warning if the recognized result differs from the retrieved information. The tomographic image generating system 100 may then determine the imaging conditions in Step S24 and the reconstructing conditions in Step S26 based on the recognized site of the subject H and the imaging direction. The subject H has a larger thickness in the depth (z-axis) direction in a side view (the subject H faces in the x-direction) than in a front view (the subject H faces in the z-direction). The subject H has a smaller two-dimensional shape (area in xy-plane or tomographic cross-section) in a side view than in a front view. By determining the reconstructing conditions and/or the reconstructed images on the basis of the site and the imaging direction, the conditions can be more precisely determined in consideration of the thickness of the subject H depending on the imaging direction and/or the area of the subject H in the tomographic cross-section.

The imaging conditions determined by the site of the subject H and the imaging direction include the imaging conditions determined on the basis of the site of the subject H described above and the rotation center O. Since the thickness of the subject H is partly determined by the site and the imaging direction, this configuration can determine the rotation center O on the basis of the thickness determined by the site and the imaging direction.

The storage section 95 may preliminarily store a table of the correspondence between the site of the subject H and the imaging direction and each imaging condition. The control section 91 may determine the imaging conditions in reference to this table.

Reconstructing conditions determined by the site of the subject H and the imaging direction include the reconstructing conditions determined on the basis of the site of the subject H described above. The storage section 95 may also preliminarily store a table of the correspondence between the site of the subject H and the imaging direction and each reconstructing condition. The control section 91 may determine the reconstructing conditions in reference to this table.

The scope of the present invention should not be limited to the first to the third embodiments and the variation described above. A tomographic image generating system according to the present invention may have any embodiment or variation, other than these preferred examples.

For example, the control section 91 may establish correspondences between the two-dimensional images and/or distance images (alternatively, the typical value of the thickness of the subject H, etc.) acquired with the three-dimensional camera 70 and the patient and site information on the subject H, and may store such correspondences on the storage section 95 or any other storing member (e.g. the PACS) connected by the communication section 94 via the network N2. If the patient and site information on an object to be imaged are entered from the operation section 92 and the storage section 95 or the other storing member connected via the network N2 previously stores the information such as the two-dimensional images and distance images corresponding to the entered patient and site information, the control section 91 may determine the imaging conditions and/or the reconstructing conditions using the stored information corresponding to the entered patient and site information without taking imaging with the three-dimensional camera 70. This configuration eliminates the need for re-imaging and re-measuring the subject with the three-dimensional camera, leading to efficient imaging. For example, the patient information and the site information on an object to be imaged may be retrieved by the communication section 94 via the network N2 from the HIS, the RIS or any other system, other than entering by the operation section 92. Alternatively, the storage section 95 may store the determined imaging conditions and/or the reconstructing conditions in connection with the patient information and the site information on a subject. This configuration enables radiographers to take images and create reconstructed images under the same conditions as before readily and efficiently.

In the embodiments described above, the imaging and the reconstructing conditions are preferably determined on the basis of the two-dimensional image (two-dimensional shape of the subject) or the distance image (thickness of the subject) captured with the three-dimensional camera 70. Instead, either one of the imaging and the reconstructing conditions may be determined. Alternatively, the imaging conditions and/or the reconstructing conditions may be determined on the basis of both the two-dimensional image (two-dimensional shape of the subject) and the distance image (thickness of the subject).

In the embodiments described above, the radiation detector F is portable (also called cassette-type), and the portable radiation detector F is placed on the detector loader 51 (refer to FIG. 1) of the imaging bed 50 in the radiographic imaging apparatus 1 for radiation tomographic imaging, for example. The present invention should also be applied to any exclusive radiation detector integrated with the imaging bed 50, other than the portable radiation detector F.

In the embodiments described above, the radiographic imaging apparatus 1 radiographs the subject in a lying posture. The radiographic imaging apparatus 1 may radiograph the subject in a standing posture.

In the embodiments described above, the radiographic imaging apparatus 1 preferably moves the radiation source 61 and the radiation detector F in mutually opposite directions to perform tomosynthesis imaging. Instead, the radiographic imaging apparatus 1 may fix the radiation detector F while moving the radiation source 61. Alternatively, the radiographic imaging apparatus 1 may fix the radiation source 61 while moving the radiation detector F.

Computer-readable media such as a hard disk drive and nonvolatile semiconductor memory store programs according to the embodiments of the present invention. The computer-readable media may be CD-ROM and any portable recording media, other than these examples described above. Alternatively, the programs according to the embodiments of the present invention may be sent through a carrier wave using a communications line.

The scope of the present invention should include various modifications and variations of specific compositions and detailed operations shown in the tomographic image generating system described above without deviating from the gist of the present invention.

The present U.S. patent application claims a priority under the Paris Convention of Japanese patent application No. 2014-147451 filed on Jul. 18, 2014, in which all contents of this application are disclosed, and which shall be a basis of correction of an incorrect translation.

What is claimed is:

1. A tomographic image generating system comprising:
    an imaging member that includes a radiation source for emitting radiation to a subject, a radiation detector including a two-dimensional array of radiation detecting elements each detecting the radiation to generate an electrical signal, the radiation detector acquiring a projected image in proportion to the emitted radiation, and a subject table for holding the subject, the subject table being disposed between the radiation source and the radiation detector, and that captures the projected image a predetermined number of times while changing a positional relationship between the radiation source and the radiation detector;
    a reconstructing member that generates a tomographic image of the subject from the projected image captured by the imaging member;
    an acquiring member that acquires a thickness of the subject and a two-dimensional shape of a surface of the subject, the surface of the subject being irradiated with radiation; and
    a controlling member that determines an imaging condition for the imaging member and/or a reconstructing condition for the reconstructing member generating the tomographic image of the subject, on the basis of the thickness and the two-dimensional shape of the surface of the subject acquired by the acquiring member.

2. The tomographic image generating system of claim 1, wherein the controlling member determines an irradiation field of the radiation source on the basis of the two-dimensional shape of the surface of the subject acquired by the acquiring member.

3. The tomographic image generating system of claim 1, wherein the controlling member determines at least one reconstructing condition selected from the group consisting of a slice pitch, a parameter for determining a tomographic slice thickness, and a number of iteration in Iterative Reconstruction, on the basis of a typical value of the thickness of the subject acquired by the acquiring member.

4. The tomographic image generating system of claim 3, wherein the controlling member further determines a value of a detection probability to be used for generating the tomographic image of the subject by the Iterative Reconstruction by the reconstructing member, on the basis of the typical value of the thickness of the subject acquired by the acquiring member.

5. The tomographic image generating system of claim 1, wherein the controlling member determines at least one reconstructing condition selected from the group consisting of an in-plane resolution, a slice pitch, a parameter for determining a tomographic slice thickness, and a number of iteration in Iterative Reconstruction, on the basis of a distribution of the thickness of the subject acquired by the acquiring member.

6. The tomographic image generating system of claim 5, wherein the controlling member further determines a value of a detection probability to be used for generating the tomographic image of the subject by the Iterative Reconstruction by the reconstructing member, on the basis of the distribution of the thickness of the subject acquired by the acquiring member.

7. The tomographic image generating system of claim 6, wherein the controlling member further specifies an area containing no subject in the tomographic image to set a predetermined value to a pixel value of the specified area, on the basis of the distribution of the thickness of the subject acquired by the acquiring member.

8. The tomographic image generating system of claim 1, wherein the controlling member determines at least one reconstructing condition selected from the group consisting of an in-plane resolution, and a number of iteration in Iterative Reconstruction, on the basis of the two-dimensional shape of the surface of the subject acquired by the acquiring member.

9. The tomographic image generating system of claim 8, wherein the controlling member further specifies an area containing no subject in the tomographic image to set a predetermined value to a pixel value of the specified area, on the basis of the two-dimensional shape of the surface of the subject acquired by the acquiring member.

10. The tomographic image generating system of claim 1, wherein the controlling member recognizes a site of the subject on the basis of the two-dimensional shape of the surface of the subject acquired by the acquiring member, and determines the imaging condition for the imaging member and/or the reconstructing condition for the reconstructing member on the basis of the recognized site.

11. The tomographic image generating system of claim 10, wherein the controlling member recognizes the site of the subject and an imaging direction on the basis of the two-dimensional shape of the surface of the subject acquired by the acquiring member, and determines the imaging condition for the imaging member and/or the reconstructing condition for the reconstructing member generating the tomographic image of the subject, on the basis of the recognized site and imaging direction.

12. The tomographic image generating system of claim 10, wherein the controlling member determines, as the imaging condition, at least one of a swing angle of the radiation source, travel speeds of the radiation source and the radiation detector, a rotation center, a number of times of imaging, a Source Image receptor Distance (SID), a radiation integration time of the radiation detector, an irradiation time per projection, and a binning size of the radiation detector.

13. The tomographic image generating system of claim 10, wherein the controlling member determines, as the reconstructing condition, at least one of an in-plane resolution, a slice pitch, a parameter for determining a tomographic slice thickness, a parameter for determining a sharpness and/or granularity, and a number of iteration in Iterative Reconstruction.

14. The tomographic image generating system of claim 1, further comprising;
a storing member that stores information on the thickness and/or the two-dimensional shape of the surface of the subject acquired by the acquiring member in association with patient information and site information on the subject; and
a retrieving member that retrieves the patient information and the site information on the subject who is to be imaged,
wherein when the storing member stores information corresponding to the patient information and the site information on the subject who is to be imaged, the controlling member determines the imaging condition and/or the reconstructing condition using the information on the thickness and/or the two-dimensional shape of the surface of the subject stored in the storing member in association with the patient information and the site information on the subject who is to be imaged, without acquisition by the acquiring member.

15. A tomographic image generating system comprising:
an imaging member that includes a radiation source for emitting radiation to a subject, a radiation detector including a two-dimensional array of radiation detecting elements each detecting the radiation to generate an electrical signal, the radiation detector acquiring a projected image in proportion to the emitted radiation, and a subject table for holding the subject, the subject table being disposed between the radiation source and the radiation detector, and that captures the projected image a predetermined number of times while changing a positional relationship between the radiation source and the radiation detector;
a reconstructing member that generates a tomographic image of the subject from the projected image captured by the imaging member;
an acquiring member that acquires a thickness of the subject and/or a two-dimensional shape of a surface of the subject, the surface of the subject being irradiated with radiation; and
a controlling member that determines an imaging condition for the imaging member and/or a reconstructing condition for the reconstructing member generating the tomographic image of the subject, on the basis of the thickness and/or the two-dimensional shape of the surface of the subject acquired by the acquiring member;
wherein the controlling member determines at least one imaging condition selected from the group consisting of travel speeds of the radiation source and the radiation detector, a rotation center, a number of times of imaging, a radiation integration time of the radiation detector, and an irradiation time per projection, on the basis of a typical value of the thickness of the subject acquired by the acquiring member.

16. A tomographic image generating system comprising:
an imaging member that includes a radiation source for emitting radiation to a subject, a radiation detector including a two-dimensional array of radiation detecting elements each detecting the radiation to generate an electrical signal, the radiation detector acquiring a projected image in proportion to the emitted radiation, and a subject table for holding the subject, the subject table being disposed between the radiation source and the radiation detector, and that captures the projected image a predetermined number of times while changing a positional relationship between the radiation source and the radiation detector;
a reconstructing member that generates a tomographic image of the subject from the projected image captured by the imaging member;
an acquiring member that acquires a thickness of the subject and/or a two-dimensional shape of a surface of the subject, the surface of the subject being irradiated with radiation; and
a controlling member that determines an imaging condition for the imaging member and/or a reconstructing condition for the reconstructing member generating the tomographic image of the subject, on the basis of the thickness and/or the two-dimensional shape of the surface of the subject acquired by the acquiring member;
wherein the controlling member determines at least one imaging condition selected from the group consisting of an irradiation field of the radiation source, travel speeds of the radiation source and the radiation detector, a rotation center, a number of times of imaging, a radiation integration time of the radiation detector, and an irradiation time per projection, on the basis of a distribution of the thickness of the subject acquired by the acquiring member.

* * * * *